US012611657B2

(12) United States Patent
Wu et al.

(10) Patent No.:    US 12,611,657 B2
(45) Date of Patent:    Apr. 28, 2026

(54) LANTHANUM OXYCARBONATE CATALYST, AND PREPARATION METHOD THEREFOR AND APPLICATION THEREOF

(71) Applicants: CHINA PETROLEUM & CHEMICAL CORPORATION, Beijing (CN); SINOPEC (BEIJING) RESEARCH INSTITUTE OF CHEMICAL INDUSTRY CO., LTD., Beijing (CN)

(72) Inventors: Jiehua Wu, Beijing (CN); Dongbing Liu, Beijing (CN); Wei Xue, Beijing (CN)

(73) Assignees: CHINA PETROLEUM & CHEMICAL CORPORATION, Beijing (CN); SINOPEC (BEIJING) RESEARCH INSTITUTE OF CHEMICAL INDUSTRY CO., LTD., Beijing (CN)

( * ) Notice: Subject to any disclaimer, the term of this patent is extended or adjusted under 35 U.S.C. 154(b) by 202 days.

(21) Appl. No.: 18/561,322

(22) PCT Filed: Nov. 3, 2021

(86) PCT No.: PCT/CN2021/128450
§ 371 (c)(1),
(2) Date: Nov. 16, 2023

(87) PCT Pub. No.: WO2022/242047
PCT Pub. Date: Nov. 24, 2022

(65) Prior Publication Data
US 2024/0246066 A1      Jul. 25, 2024

(30) Foreign Application Priority Data
May 21, 2021    (CN) ......................... 202110561190.4

(51) Int. Cl.
*B01J 27/232*      (2006.01)
*B01J 35/30*      (2024.01)
(Continued)

(52) U.S. Cl.
CPC ........... *B01J 27/232* (2013.01); *B01J 35/395* (2024.01); *B01J 35/50* (2024.01); *B01J 35/70* (2024.01);
(Continued)

(58) Field of Classification Search
CPC ........ B01J 27/232; B01J 35/395; B01J 35/50; B01J 35/70; B01J 37/04; B01J 37/10;
(Continued)

(56) References Cited

U.S. PATENT DOCUMENTS

| | | | |
|---|---|---|---|
| 4,929,787 A | 5/1990 | Cameron et al. | |
| 10,322,409 B1 * | 6/2019 | Zahir | ................. B01D 53/9413 |

(Continued)

FOREIGN PATENT DOCUMENTS

| | | |
|---|---|---|
| CN | 1061730 A | 6/1992 |
| CN | 1074391 A | 7/1993 |

(Continued)

OTHER PUBLICATIONS

Khomchenko I.G., "General Chemistry", Novaya Volna, 1997, Moscow, pp. 19.

(Continued)

*Primary Examiner* — Prem C Singh
*Assistant Examiner* — Francis C Campanell
(74) *Attorney, Agent, or Firm* — NKL Law; Allen Xue

(57)      ABSTRACT

A lanthanum oxycarbonate catalyst, and a preparation method therefor and an application thereof are provided. The lanthanum oxycarbonate catalyst contains a rod-shaped lanthanum oxycarbonate catalyst and a substantially parallelepiped lanthanum oxycarbonate catalyst. The lanthanum (Continued)

oxycarbonate catalyst can be used for efficiently performing a methane oxidative coupling reaction at a relatively low temperature.

26 Claims, 4 Drawing Sheets

(51) Int. Cl.

| | |
|---|---|
| *B01J 35/50* | (2024.01) |
| *B01J 35/70* | (2024.01) |
| *B01J 37/04* | (2006.01) |
| *B01J 37/10* | (2006.01) |
| *B01J 37/34* | (2006.01) |
| *C07C 2/84* | (2006.01) |

(52) U.S. Cl.
CPC ............... *B01J 37/04* (2013.01); *B01J 37/10* (2013.01); *B01J 37/343* (2013.01); *C07C 2/84* (2013.01); *B01J 2235/15* (2024.01); *B01J 2235/30* (2024.01)

(58) Field of Classification Search
CPC .. B01J 37/343; B01J 2235/15; B01J 2235/30; B01J 23/10; B01J 35/45; B01J 35/54; B01J 37/031; C07C 2/84; Y02P 20/52
USPC ........................................................ 585/708
See application file for complete search history.

(56) References Cited

U.S. PATENT DOCUMENTS

| | | | |
|---|---|---|---|
| 2012/0065443 A1 | 3/2012 | Mabande et al. |
| 2018/0353940 A1 | 12/2018 | Liang et al. |
| 2020/0238256 A1 | 7/2020 | Zurcher et al. |

FOREIGN PATENT DOCUMENTS

| | | |
|---|---|---|
| CN | 102936028 A | 2/2013 |
| CN | 103011242 A | 4/2013 |
| CN | 105749892 A | 7/2016 |
| CN | 109663587 A | 4/2019 |
| CN | 109999871 A | 7/2019 |
| CN | 110026199 A | 7/2019 |
| CN | 110694583 A | 1/2020 |
| RU | 2553265 C2 | 6/2015 |

OTHER PUBLICATIONS

Chen, Jie et al.; "Study on the synthesis of glycerol carbonate from glycerol by La2O2CO3 based catalyst"; Chinese Selected Doctoral Dissertations and Mater's Theses Full-Text Databases(Doctoral), engineering Science & Technology I; vol. 12; Dec. 15, 2015; ISSN:1674-0246; pp. 1-23.

Li, Zhe et al.; "Oxidative Coupling of Methane Over La2O3 Catalysts a Comparison of La2O3 Catalysts From Different Preparation Methods"; Journal of Fuel Chemistry and Technology; vol. 24, No. 3; Jun. 1996; pp. 191-197.

Wang, Fei et al.; "La(OH)3 and La2O2CO3 nanorod catalysts for Claisen-Schmidt condensation"; Chinese Journal of Catalysis; vol. 35, No. 3; Mar. 20, 2014; pp. 437-443.

Li, Guogang et al.; "Eu3+/Tb3+-Doped La2O2CO3/La2O3 Nano/Microcrystals with Multiform Morphologies: Facile Synthesis, Growth Mechanism, and Luminescence Properties"; Inorg. Chem.; vol. 49, No. 22; Year: 2010, pp. 10522-10535.

Yang, Xiaoyan et al.; "LaCO3OH microstructures with tunable morphologies: EDTA-assisted hydrothermal synthesis, formation mechanism and adsorption properties"; RSC Advances, vol. 3; Year: 2013, pp. 3907-3916.

Hou, Yu-Hui et al.; "Structure Sensitivity of La2O2CO3 Catalysts in the Oxidative Coupling of Methane"; ACS Catalysis; vol. 5; Feb. 2, 2015; pp. 1663-1674.

Wang, Hengxiu et al.; "Study on Oxidative Coupling of Methane Over Various Lanthanum Compounds"; Chemical Reaction Engineering and Technology; vol. 13, No. 3; Sep. 1997; pp. 1-6.

* cited by examiner

LANTHANUM OXYCARBONATE CATALYST, AND PREPARATION METHOD THEREFOR AND APPLICATION THEREOF

CROSS REFERENCE TO RELATED APPLICATIONS

This application is a U.S. national stage entry of PCT International Application No. PCT/CN2021/128450, filed on Nov. 3, 2021, which claims the priority of the Chinese Patent Application No. "202110561190.4", filed on May 21, 2021, the content of which is incorporated herein by reference in its entirety.

TECHNICAL FIELD

The invention relates to the technical field of catalyst, in particular to a lanthanum oxycarbonate catalyst, and a preparation method therefor and an application thereof.

BACKGROUND ART

The methane oxidative coupling for producing hydrocarbons containing 2 or more carbon atoms is one of the most challenging and attractive research topics in the catalytic field at present due to its academic significance and potentially huge economic value. Since the publication of a thesis by the authors Keller and Bhasin in 1982, the methane oxidative coupling has been the focus of attention in the catalytic and chemical industries and the oil and natural gas field. The methane oxidative coupling is an exothermic reaction, and the generated products are mainly water and the hydrocarbons containing 2 or more carbon atoms, the technology exhibits the characteristics of desirable atomic economy and environmental friendly performance, it has been the object of competitive researches and studies in various scientific research institutions and large enterprises during the last four decades, the researchers have made many explorations on the development of catalysts, however, due to the problems concerning existence of the catalyst or its service life, or the properties of catalysts need to be improved, the catalyst with an industrialization level has not been put into the market, the research and improvement of catalysts require the continuous exploration.

The research by Zhe Li, et al (*Journal of Dye Chemistry*, 1996, Vol. 24, No. 3, pp. 191-197) considered that the lanthanum oxide was used as a methane oxidative coupling catalyst, the different preparation methods caused the various results, which were associated with the surface defect sites, adsorbed oxygen species, and surface alkaline and acidic sites; Fei Wang et al. (*Chinese Journal of Catalysis*, No. 35; 2014; pp. 437-443) mentioned in the application of La(OH)$_3$ and La$_2$O$_2$CO$_3$ nanorod catalysts in Claisen-Schmidt condensation reaction that the rod-shaped lanthanum hydroxide and lanthanum oxycarbonate were prepared by the hydrothermal method, the lanthanum oxide was dissolved in nitric acid solution, the pH was adjusted to 7-13 with potassium hydroxide having a concentration of 9 mol/L, the product was subjected to drying to obtain the sample of lanthanum hydroxide, which was further roasted to prepare the sample of lanthanum oxycarbonate, the article believed that a pH of said solution affected the length-diameter ratio of the product lanthanum oxycarbonate, the greater was the alkalinity, the larger was the length-diameter ratio, when a pH of said solution was 13, the length-diameter ratio of the nanorods of the prepared lanthanum oxycarbonate reached 20 or more; Guogang Li, et al. (*Inorg. Chem.*, 2010, No. 49, pp. 10522-10535) mentioned the preparation method and growth mechanism of Eu3+/Tb3+ coated lanthanum oxycarbonate and lanthanum oxide microcrystals in the application field of luminescent materials, the lanthanum oxide and lanthanum oxycarbonate materials with different morphologies were prepared by using the co-precipitation method, it was recited in the article that carbon sources and the pH were the main factors affecting the morphology of materials, when urea was used as the carbon source, and the pH was controlled to 7, the diamond-shaped LaCO$_3$OH can be obtained; when the pH was raised to 10, the morphology of the material was changed to the sandwich shape, the material was calcined at 600° C. for 4 hours to generate La$_2$O$_2$CO$_3$; when the different carbon sources were used, a pH of the solution was controlled to be the same, and the lanthanum compound materials with different morphologies were obtained. Xiaoyan Yang, et al. (*RSC Adv.*, 2013, No. 3, pp. 3907-3916) proposed that LaCO$_3$OH with different morphologies may be prepared through the hydrothermal method by using urea as the carbon source and controlling the reaction conditions under the premise of adding Ethylene Diamine Tetraacetic Acid (EDTA). The China Patent CN109999871A discloses a preparation method of La$_2$O$_2$CO$_3$ nano triangular plate loaded Pd catalyst and its application in the hydrogenation reaction process of cinnamyl aldehyde, wherein the potassium carbonate is dissolved in ethylene glycol solution. The China Patent CN109663587A discloses a preparation method of flower-like lanthanum oxide-based nano-microspheres and its application in a methane oxidative coupling reaction, the flower-like lanthanum oxide-based nano-microspheres are prepared by hydrothermal crystallization method, organic sugars and organic acids are required in the preparation method, so the cost of raw materials is high. Hui-Lin Wan, et al. (Structure Sensitivity of La$_2$O$_2$CO$_3$ Catalysts in the Oxidative Coupling of Methane, *ACS Catal.*, 2015, No. 5, pp. 1663-1674) reports the performance of the rod-shaped lanthanum oxycarbonate prepared with the hydrothermal method in the methane oxidative coupling reaction, the preparation methods are different although the same hydrothermal method is used, the obtained rod-shaped lanthanum oxycarbonate in the process of producing hydrocarbons containing 2 or more carbon atoms through the methane oxidative coupling reaction have significantly different properties, both the operation process and preparation conditions influence the morphology and catalytic performance of the lanthanum oxycarbonate.

The prior art neither mentions how to prepare a catalyst comprising a rod-shaped lanthanum oxycarbonate and a substantially parallelepiped lanthanum oxycarbonate with a simple and low-cost operation, nor discuss an influence of the catalyst comprising both the rod-shaped lanthanum oxycarbonate and the substantially parallelepiped lanthanum oxycarbonate on the catalytic performance.

SUMMARY OF THE INVENTION

The present invention aims to overcome the above-mentioned defects of the prior art, and provides a lanthanum oxycarbonate catalyst comprising a rod-shaped lanthanum oxycarbonate and a substantially parallelepiped lanthanum oxycarbonate, a preparation method therefor and a use thereof. The lanthanum oxycarbonate catalyst provided by the present invention can be used for efficiently performing a methane oxidative coupling reaction at a relatively low temperature.

In order to fulfill the above objects, a first aspect the present invention provides a lanthanum oxycarbonate ($La_2O_2CO_3$) catalyst comprising a substantially parallelepiped lanthanum oxycarbonate.

A second aspect of the invention provides a method for preparing the lanthanum oxycarbonate catalyst comprising:

step 1: adding an alkaline solution into a lanthanum-containing compound solution at a temperature not higher than 20° C.;

step 2: subjecting the mixed materials obtained from step 1 to a hydrothermal reaction;

step 3: subjecting the solid material obtained after separation of materials from the hydrothermal reaction to drying and roasting in sequence, thereby preparing the lanthanum oxycarbonate catalyst.

A third aspect of the invention provides the lanthanum oxycarbonate catalyst prepared with the aforementioned method.

A fourth aspect of the present invention provides a use of the aforesaid lanthanum oxycarbonate catalyst in the methane oxidative coupling reaction for producing hydrocarbons containing 2 or more carbon atoms.

A fifth aspect of the present invention provides a method for preparing hydrocarbons containing 2 or more carbon atoms with methane comprising: subjecting the methane and the aforesaid lanthanum oxycarbonate catalyst to a contact reaction in the presence of oxygen gas under the conditions of methane oxidative coupling reaction;

alternatively, preparing a lanthanum oxycarbonate catalyst with the aforesaid method, then subjecting the methane and the obtained lanthanum oxycarbonate catalyst to a contact reaction in the presence of oxygen gas under the conditions of methane oxidative coupling reaction.

The present invention proposes a catalyst comprising a substantially parallelepiped lanthanum oxycarbonate for the first time, the catalyst is prepared through a single step of a hydrothermal method by using the operation of adding an alkaline solution under a low temperature (not higher than 20° C.) to control the nucleation and growth conditions, thus the method is simple and convenient. The content of the substantially parallelepiped lanthanum oxycarbonate contained in the catalyst can be regulated by precisely controlling the nucleation and growth conditions (e.g., controlling the rate of adding the alkaline solution and the temperature).

The present inventors have discovered in the researches that the lanthanum oxycarbonate catalysts with different morphologies have slightly different catalytic activity in the methane oxidative coupling reaction; the catalyst comprising a rod-shaped lanthanum oxycarbonate and a substantially parallelepiped lanthanum oxycarbonate provided by the present invention has a characteristic of efficiently performing a methane oxidative coupling reaction under a low temperature; as compared with the performance of a rod-shaped catalyst prepared with the method in the Literature Hui-Lin Wan, et al (Structure Sensitivity of $La_2O_2CO_3$ Catalysts in the Oxidative Coupling of methane, *ACS Catal.*, 2015, No. 5, pp. 1663-1674), wherein the methane conversion ratio is 30.5%, the C2 hydrocarbon selectivity is 48.6%, the C2 hydrocarbon yield is 14.8%, when the catalyst is evaluated in the Literature under the following conditions: the total hourly space velocity of 30,000 mL/(g·h), the methane hourly space velocity of 22,500 mL/(g·h), a molar ratio of methane to oxygen gas being 3:1, and the temperature of 500° C.; in contrast, the catalyst prepared in Example 1 of the present invention exhibits that the methane conversion ratio is 33.5%, the C2 hydrocarbon selectivity is 44.9%, the C2 hydrocarbon yield is 15.04%, when the catalyst is evaluated under the following conditions: the total hourly space velocity of 30,000 mL/(g·h), the methane hourly space velocity of 22,500 mL/(g·h), a molar ratio of methane to oxygen gas being 3:1, and the temperature of 500° C. Furthermore, the catalyst of the present invention has superior catalytic performance at a methane hourly space velocity within a range of 30,000 mL/(g·h)–150,000 mL/(g·h), the specific results are as follows: the catalyst of the present invention can achieve the C2 hydrocarbon yield of 12% at 520° C. when the methane hourly space velocity is 120,000 mL/(g·h), and a molar ratio of methane to oxygen gas being 8:1, while the rod-shaped catalyst of the Literature achieves the C2 hydrocarbon yield at 550° C. under the same conditions, thus the temperature of the catalyst of the present invention is 30° C. lower than the temperature of the rod-shaped catalyst in the Literature.

(2) According to the present invention, when the catalyst comprises a substantially parallelepiped lanthanum oxycarbonate, the catalyst has more active oxygen defect sites and types of active oxygen, thereby exhibiting a desirable reaction activity in a methane oxidative coupling reaction, and achieving a higher methane conversion rate and selectivity of hydrocarbons containing 2 or more carbon atoms; since the main exposed surface of the lanthanum oxycarbonate having a substantially parallelepiped structure is a high index crystal surface, the unsaturation level of the atomic coordination of the high index crystal surface is relatively high, there are more vacancies, the lanthanum oxycarbonate has a high proportion of peroxy and superoxide species and a high density of alkaline sites, thus the surface activity is higher. In addition, the lanthanum oxycarbonate catalyst comprising a substantially parallelepiped lanthanum oxycarbonate provided by the present invention further exhibits excellent catalytic stability, which is specifically embodied in that the catalysts prepared in the Examples have stable performance after subjecting to the performance test over a service life of 550 h.

The lanthanum oxycarbonate catalyst comprising a substantially parallelepiped lanthanum oxycarbonate prepared in the present invention may perform nucleation and growth under the alkaline condition of low temperature, absorb carbon dioxide in the air, and is roasted to prepare a lanthanum oxycarbonate catalyst, which is capable of producing a selectivity of C2 hydrocarbon being 50% or more when controlling the methane hourly space velocity within a range of 30,000 mL/(g·h)–150,000 mL/(g·h) and controlling the ratio of methane to the oxygen gas to be 5-8:1, or even producing the selectivity of C2 hydrocarbon being 60% or more under the optimized conditions, thus the selectivity of C2 hydrocarbon is high; in addition, the catalyst has a low selectivity of the byproducts carbon monoxide and carbon dioxide, which reduces the occurrence of deep oxidation reactions, decreases the transient heat release, lowers the difficulty in the heat removal operations after amplification of the reactor, the catalyst produces a high selectivity of C2 hydrocarbon under the condition of high hourly space velocity, thereby providing a technical support for the industrial application of the methane oxidative coupling reaction process for producing hydrocarbons containing 2 or more carbon atoms.

DESCRIPTION OF THE PREFERRED EMBODIMENT

Figure 1:
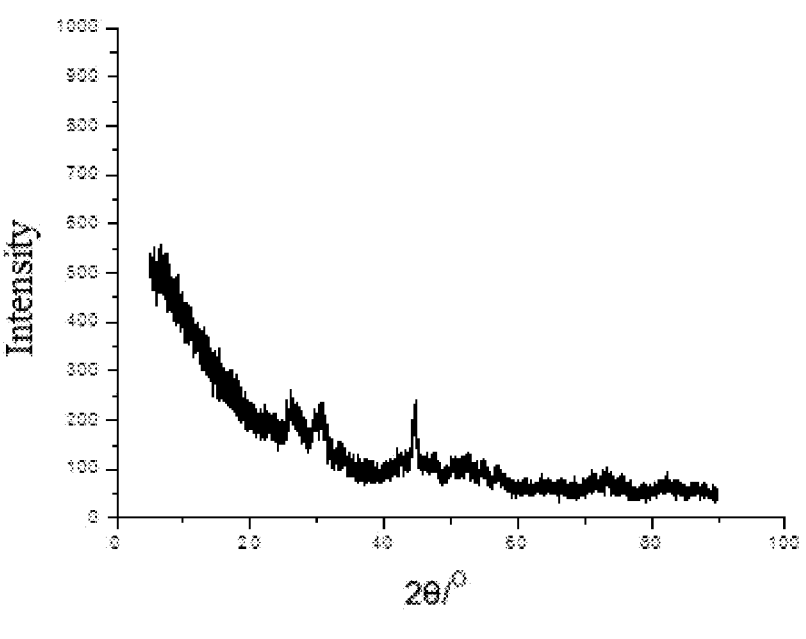
FIG. 1 illustrates an X-ray (XRD) spectrogram of the methane oxidative coupling catalyst prepared in Example 1.

In a first aspect, the present invention provides a lanthanum oxycarbonate catalyst comprising a substantially parallelepiped lanthanum oxycarbonate.

According to the present invention, the term "substantially parallelepiped" comprises a cross section that is parallelogram in shape, e.g., a quadrilateral that is similar to a parallelogram. That is, the sum of two adjacent interior angles of the substantially parallelepiped is equal to or close to 180°.

Preferably, two adjacent interior angles of the substantially parallelepiped are denoted as $\angle A$ and $\angle B$, wherein $\angle A$ is set as an acute angle and $\angle B$ is set as an obtuse angle, $60° < \angle A < 90°$, and $170° < (\angle A + \angle B) < 195°$. For example, $\angle A$ may be 65°, 68°, 70°, 72°, 75°, 78°, 80°, 82°, 85°, 88°. $\angle A + \angle B$ may be 172°, 175°, 178°, 180°, 182°, 185°, 188°, 190°, 193°.

The angles can be measured by a scanning electron microscope equipped with an angular measurement scaleplate.

According to the invention, a side length of the substantially parallelepiped may vary within a wide range, preferably within a range of 1 μm-5 μm, for example, 1 μm, 2 μm, 3 μm, 4 μm, 5 μm, more preferably within a range of 1.5 μm-3.5 μm.

The side length can be measured by a scanning electron microscope equipped with a measurement scaleplate.

According to the invention, it is preferred that the thickness of the substantially parallelepiped lanthanum oxycarbonate may vary within a wide range, preferably within a range of 100 nm-500 nm, for example, 100 nm, 200 nm, 300 nm, 400 nm, 500 nm, more preferably 200 nm-400 nm.

The thickness may be measured by a scanning electron microscope equipped with a measurement scaleplate.

According to the present invention, the content of the substantially parallelepiped lanthanum oxycarbonate in the lanthanum oxycarbonate catalyst may vary within a wide range, preferably, the content of the substantially parallelepiped lanthanum oxycarbonate is equal to or higher than 0.01 wt %, such as 0.01 wt %, 0.02 wt %, 0.04 wt %, 0.05 wt %, 0.1 wt %, 0.5 wt %, 1 wt %, 2 wt %, 3 wt %, 4 wt %, 5 wt %, 6 wt %, 7 wt %, 8 wt %, 9 wt %, 10 wt %, 15 wt %, 20 wt %, 25 wt %, 30 wt %, 35 wt %, 40 wt %, 45 wt %, 50 wt %, more preferably within a range of 0.1-50 wt %, further preferably within a range of 0.2-45 wt %, still further preferably within a range of 0.6-40 wt %, based on the total weight of the lanthanum oxycarbonate catalyst.

The content of lanthanum oxycarbonate with a substantially parallelepiped structure in the lanthanum oxycarbonate catalyst is calculated based the area of the substantially parallelepiped structure of lanthanum oxycarbonate on the electron microscope image. Typically, 3-5 electron microscope fields are taken, and the areas measured in the 3-5 fields are averaged as the content of lanthanum oxycarbonate with the substantially parallelepiped structure.

According to the present invention, the lanthanum oxycarbonate catalyst further comprises a rod-shaped lanthanum oxycarbonate.

The present invention does not impose specific limitation to the length of the rod-shaped lanthanum oxycarbonate, as long as it conforms to the nanostructure, and preferably, the length is within a range of 50 nm-500 nm, the length may be, for example, 50 nm, 100 nm, 150 nm, 200 nm, 250 nm, 300 nm, 350 nm, 400 nm, 450 nm, 500 nm, and more preferably within a range of 95 nm-450 nm.

The "length" means the linear distance between the two-end points with a longest distance, the distance can be measured by a measurement scaleplate of the scanning electron microscope.

The diameter of the rod-shaped lanthanum oxycarbonate is not particularly limited in the invention, as long as it conforms to a nanostructure, and preferably, its diameter is within a range of 15 nm-40 nm, it may be, for example, 15 nm, 18 nm, 20 nm, 22 nm, 24 nm, 26 nm, 28 nm, 30 nm, 32 nm, 34 nm, 35 nm, 38 nm, 40 nm, and more preferably within a range of 15 nm-35 nm.

The "diameter" refers to that the maximum length of a cross-sectional circumscribed circle in any section among the sections perpendicular to the axis; the distance can be measured by a measurement scaleplate of the scanning electron microscope.

According to the present invention, a mass ratio of the substantially parallelepiped lanthanum oxycarbonate to the rod-shaped lanthanum oxycarbonate may vary within a wide range, preferably, the mass ratio of the substantially parallelepiped lanthanum oxycarbonate to the rod-shaped lanthanum oxycarbonate is 1:100, and for example, it may be 1:1, 1:10, 1:20, 1:30, 1:40, 1:50, 1:60, 1:70, 1:80, 1:90, 1:100, more preferably 1:2-50, further more preferably 1:5-40, and even more preferably 1:6-12.

Wherein the mass ratio of the lanthanum oxycarbonate with a substantially parallelepiped structure to the lanthanum oxycarbonate with a rod-shaped structure is calculated based on the area ratio of the two morphologies of the catalyst on the SEM image. Typically 3-5 SEM fields are taken and the area ratios measured in said 3-5 fields is averaged as the mass ratio of the lanthanum oxycarbonate with a substantially parallelepiped structure to the lanthanum oxycarbonate with a rod-shaped structure.

In a second aspect, the present invention provides a method for preparing the lanthanum oxycarbonate catalyst comprising:

step 1: adding an alkaline solution into a lanthanum-containing compound solution at a temperature not higher than 20° C.;

step 2: subjecting the mixed materials obtained from step 1 to a hydrothermal reaction;

step 3: subjecting the solid material obtained after separation of materials from the hydrothermal reaction to drying and roasting in sequence, thereby preparing the lanthanum oxycarbonate catalyst.

The present inventors have discovered in researches that the lanthanum oxycarbonate catalyst comprising a substantially parallelepiped lanthanum oxycarbonate is prepared by adding an alkaline solution and performing nucleation under a low temperature (not higher than 20° C.), then subjecting to a hydrothermal reaction, and subjecting the solid material obtained after separation of materials from the hydrothermal reaction to drying and roasting in sequence, the lanthanum oxycarbonate catalyst comprising a substantially parallelepiped lanthanum oxycarbonate can obtain a similar yield of hydrocarbons containing 2 or more carbon atoms in the process of producing hydrocarbons containing 2 or more carbon atoms through the methane oxidative coupling reaction at a temperature 20-50° C. lower than that of the lanthanum oxycarbonate catalyst with a rod-shape structure.

According to the present invention, the temperature in step 1 is preferably within a range of 1° C.-20° C., more preferably within a range of 5° C.-18° C., further preferably within a range of 8° C.-12° C., and the resulting substantially parallelepiped oxycarbonate catalyst has a better catalytic effect at low reaction temperatures within the preferred temperature range.

According to the present invention, it is preferred that the alkaline solution in step 1 is added dropwise till the obtained mixed material has a pH of 9-13, for example, the pH may be 9, 9.5, 10, 10.5, 11, 11.5, 12, 12.5, 13, more preferably within a range of 10-12, further preferably within a range of 11-12.

According to the present invention, in order to further obtain the lanthanum oxycarbonate catalyst with a substantially parallelepiped structure, the alkaline solution is a sodium hydroxide solution with a concentration of 5 wt % to 20 wt %, wherein the addition amount of the alkaline solution per minute is within a range of 0.01-1.5 g, for example, 0.01 g, 0.05 g, 0.1 g, 0.2 g, 0.3 g, 0.4 g, 0.5 g, 0.6 g, 0.7 g, 0.8 g, 0.9 g, 1 g, 1.1 g, 1.2 g, 1.3 g, 1.4 g, 1.5 g, preferably 0.01 g-1.25 g, more preferably 0.015 g-0.45 g, in terms of sodium hydroxide, relative to per kg of the lanthanum-containing compound solution.

According to the present invention, the alkaline solution may also be a conventional alkaline solution, such as sodium carbonate solution, sodium bicarbonate solution, potassium hydroxide solution, potassium carbonate solution, potassium bicarbonate solution, provided that it is added at such a rate that the change in hydroxyl radical (pH) in the system is consistent with the change when the alkaline solution is sodium hydroxide solution.

According to the present invention, the lanthanum compound is preferably a water-soluble lanthanum salt, which for example may include but not limited to lanthanum chloride, lanthanum chlorate and lanthanum nitrate.

Wherein the concentration of the lanthanum element in the mixed solution can be selected within a wide range, preferably, in order to prepare a lanthanum oxycarbonate catalyst with better performance, the concentration of lanthanum element in the lanthanum-containing compound solution is within a range of 0.05 wt %-10 wt %, preferably 0.2 wt %-5 wt %, more preferably 0.3 wt %-0.7 wt %.

According to the present invention, the method for preparing the lanthanum-containing compound solution may comprising: dissolving a water-soluble lanthanum salt in water under a temperature not higher than 20° C., preferably 5° C.-18° C., more preferably 8° C.-12° C. at a stirring speed within a range of 100 rpm-1000 rpm, preferably 650 rpm-850 rpm, and stirring the water-soluble lanthanum salt until dissolution.

According to the present invention, in order to further obtain the lanthanum oxycarbonate catalyst with a substantially parallelepiped structure, it is preferable to control the stirring rate during the process of adding an alkaline solution to the lanthanum-containing compound solution, in particular: in step 1, after the addition of an alkaline solution to the lanthanum-containing compound solution under conditions of maintaining stationary or performing a low speed stirring until the precipitation of solid material, the alkaline solution is further added into the lanthanum-containing compound solution under the conditions of a high speed stirring, until the alkaline solution is dropwise added completely.

Wherein the low speed stirring refers to a rotational speed equal to or lower than 300 rpm, preferably 50 rpm-300 rpm, more preferably 50 rpm-200 rpm.

The high speed stirring refers to a rotational speed equal to or larger than 800 rpm, preferably 800 rpm-1,500 rpm, more preferably 900 rpm-1,500 rpm.

According to the present invention, in order to further obtain the lanthanum oxycarbonate catalyst with a substantially parallelepiped structure, it is preferable that the method further comprising: prior to the hydrothermal reaction, stirring the mixed material at a temperature not higher than 20° C., preferably between 1° C. and 20° C., more preferably between 5° C. and 18° C., further more preferably between 8° C. and 12° C.

Wherein the rotational speed of the stirring may vary within a wide range, preferably within a range of 100 rpm-1,000 rpm, more preferably within a range of 650 rpm-850 rpm, relative to the system with a volume of 0.3 L-0.6 L.

Wherein the stirring time is preferably within a range of 5 min-60 min, preferably 10 min-30 min.

According to the present invention, for the sake of further improving the structural uniformity of the lanthanum oxycarbonate, it is preferred that the method further comprising: subjecting the mixed material to an ultrasonic treatment prior to the hydrothermal synthesis reaction. Wherein the ultrasonic treatment conditions may be selected from a wide range, and preferably including: a frequency of 20 kHz-120 kHz, for example, 20 kHz, 25 kHz, 30 kHz, 35 kHz, 40 kHz, 45 kHz, 50 kHz, 55 kHz, 60 kHz, 65 kHz, 70 kHz, 75 kHz, 80 kHz, 85 kHz, 90 kHz, 95 kHz, 100 kHz, 110 kHz, 120 kHz, preferably a frequency of 20 kHz-40 kHz; a power of 200 W-1,000 W, for example, 200 W, 300 W, 400 W, 500 W, 600 W, 700 W, 800 W, 900 W, 1,000 W, preferably a power of 400 W-800 W; a time of 20 min-100 min, for example, 20 min, 30 min, 40 min, 50 min, 60 min, 70 min, 80 min, 90 min, 100 min, preferably a time of 60 min-80 min; and a temperature of 25° C.-60° C., for example, 25° C., 27° C., 30° C., 32° C., 35° C., 38° C., 40° C., 42° C., 45° C., 48° C., 50° C., 53° C., 55° C., 58° C., 60° C., preferably 25° C.-40° C.

According to a preferred embodiment of the present invention, the method for preparing the mixed material comprising: adding an alkaline solution to the lanthanum-containing compound solution under a temperature of 8° C.-12° C. and the condition of maintaining stationary or performing a low speed stirring (the rotational speed is within a range of 50 rpm-300 rpm), the alkaline solution is the sodium hydroxide solution with a concentration of 5 wt %-20 wt %, the addition amount of the alkaline solution per minute is within a range of 0.015 g-0.045 g in terms of sodium hydroxide, relative to per kg of the lanthanum-containing compound solution; after precipitation of the solid material, the rotational speed is increased to 800 rpm-1,500 rpm, the sodium hydroxide is further added until a pH of the system is within a range of 9-13, the dropwise adding of sodium hydroxide solution is stopped to obtain the mixed material, then stirring the mixed material under a temperature of 8° C.-12° C. for 10 min-30 min at a rotational speed of 650 rpm-850 rpm (relative to the system with a volume of 0.3 L-0.6 L), followed by the ultrasonic treatment for 60 min-80 min at a power of 400 W-800 W, a frequency of 20 kHz-40 kHz and a temperature of 25° C.-40° C., thereby obtaining the mixed material.

According to the present invention, the hydrothermal reaction conditions may be conventional hydrothermal reaction conditions, however, in order to more efficiently improve the performance of the prepared lanthanum oxycarbonate catalyst, the hydrothermal reaction conditions preferably comprise a temperature of 150° C.-200° C. (e.g., it may be 150° C., 160° C., 170° C., 180° C., 190° C., 200° C.), and a time of 10 h-100 h (e.g., it may be 10 h, 20 h, 30 h, 40 h, 50 h, 60 h, 70 h, 80 h, 90 h, 100 h).

According to the present invention, the method of separation in step 3 may be filtration, centrifugation and the like. According to a preferred embodiment of the present invention, the solid material is obtained by means of centrifugation. The conditions of centrifugation preferably comprising: a rotational speed of 5,000 rpm-10,000 rpm, preferably 8,000 rpm-9,000 rpm, a time of 20 min-60 min, preferably 30 min-50 min, and a temperature not higher than 20° C., preferably 8° C.-15° C., more preferably 8° C.-12° C. The present inventors have found that the use of control conditions below 20° C. during the centrifugation process facilitates the yield of a more solid product.

According to the present invention, it is preferred that the solid material is further subjected to washing before the drying process, and water and/or ethanol may be used for washing the solid material. According to a preferred embodiment of the present invention, water (distilled water) is initially used for washing the solid material till the wash solution is neutral, the solid material is then washed with ethanol for 1-2 times.

According to the present invention, the drying temperature may vary within a wide range, the drying temperature is preferably within a range of 60° C.-100° C., for example, it may be 60° C., 70° C., 80° C., 90° C., 100° C.

According to the present invention, the drying time may change within a wide range, the drying time is preferably within a range of 12 h-24 h, for example it may be 12 h, 14 h, 16 h, 18 h, 20 h, 22 h, 24 h.

According to the present invention, the roasting temperature may be varied within a wide range, the roasting temperature is preferably within a range of 450° C.-600° C., for example it may be 450° C., 500° C., 550° C., 600° C.

According to the present invention, the roasting time can vary within a wide range, the roasting time is preferably within a range of 2 h-8 h, for example, it may be 2 h, 3 h, 4 h, 5 h, 6 h, 7 h, 8 h.

According to the present invention, the roasting atmosphere is not particularly limited, it may be an air atmosphere, a carbon dioxide atmosphere, or a nitrogen gas atmosphere, preferably an air atmosphere or a carbon dioxide atmosphere.

In a third aspect, the present invention provides a lanthanum oxycarbonate catalyst prepared with the aforementioned method.

In a fourth aspect, the invention provides a use of the aforementioned lanthanum oxycarbonate catalyst in the methane oxidative coupling reaction for producing hydrocarbons containing 2 or more carbon atoms.

According to the present invention, the catalyst of the present invention can be used in a continuous flow reactor to produce hydrocarbons containing 2 or more carbon atoms from methane (e.g., natural gas). The continuous flow reactor may be a fixed bed reactor, a stacked bed reactor, a fluidized bed reactor, a moving bed reactor, or an ebullated bed reactor. The catalyst can be arranged in layers in the continuous flow reactor (e.g., fixed bed), or mixed with the reactant stream (e.g., the ebullated bed).

In a fifth aspect, the present invention provides a method for preparing hydrocarbons containing 2 or more carbon atoms with methane comprising: subjecting the methane and the aforementioned lanthanum oxycarbonate catalyst to a contact reaction in the presence of oxygen gas under the conditions of methane oxidative coupling reaction;

alternatively, preparing a lanthanum oxycarbonate catalyst with the aforementioned method, then subjecting the methane and the obtained lanthanum oxycarbonate catalyst to a contact reaction in the presence of oxygen gas under the conditions of methane oxidative coupling reaction.

According to the present invention, the conditions of methane oxidative coupling reaction are not particularly defined therein, which may be the conventional choice in the art, for example, the conditions of methane oxidative coupling reaction may comprising: a reaction temperature of 400° C.-650° C. (e.g., 400° C., 410° C., 420° C., 430° C., 440° C., 450° C., 460° C., 470° C., 480° C., 490° C., 500° C., 550° C., 600° C., 650° C.), and a methane hourly space velocity within a range of 30,000 mL/(g·h)–150,000 mL/(g·h). Preferably, a molar ratio of the used amounts of methane and oxygen gas is within a range of 2-10:1, more preferably within a range of 3-8:1.

The lanthanum oxycarbonate catalyst provided by the present invention exhibits excellent catalytic properties in the methane oxidative coupling reaction for producing hydrocarbons containing 2 or more carbon atoms, the activation temperature of the reaction is low, the methane conversion rate is high, and the selectivity of hydrocarbons containing 2 or more carbon atoms is desirable.

1. A lanthanum oxycarbonate catalyst, the lanthanum oxycarbonate catalyst comprises a substantially parallelepiped lanthanum oxycarbonate.

2. The lanthanum oxycarbonate catalyst of the embodiment 1, wherein the substantially parallelepiped lanthanum oxycarbonate is contained in an amount equal to or higher than 0.01 wt %, preferably 0.1-50 wt %, further preferably 0.2-45 wt %, further more preferably 0.6-40 wt %, based on the total weight of the lanthanum oxycarbonate catalyst.

3. The lanthanum oxycarbonate catalyst of the embodiment 1 or 2, wherein a side length of the substantially parallelepiped is within a range of 1 μm-5 μm;

preferably, a thickness of the substantially parallelepiped lanthanum oxycarbonate is within a range of 100 nm-500 nm;

preferably, two adjacent interior angles of the substantially parallelepiped lanthanum oxycarbonate are denoted as ∠A and ∠B, wherein 60°<∠A<90°, and 170°<(∠A+∠B)<195°.

4. A lanthanum oxycarbonate catalyst, wherein the lanthanum oxycarbonate catalyst further comprises a rod-shaped lanthanum oxycarbonate.

5. The lanthanum oxycarbonate catalyst of the embodiment 4, wherein a mass ratio of the substantially parallelepiped lanthanum oxycarbonate to the rod-shaped lanthanum oxycarbonate is within a range of 1:1-100, preferably 1:2-50, more preferably 1:5-40.

6. The lanthanum oxycarbonate catalyst of the embodiment 4 or 5, wherein the rod-shaped lanthanum oxycarbonate has a length of 50 nm-500 nm and a diameter of 15 nm-40 nm.

7. A method for preparing the lanthanum oxycarbonate catalyst comprising:

step 1: adding an alkaline solution into a lanthanum-containing compound solution at a temperature not higher than 20° C.;

step 2: subjecting the mixed materials obtained from Step 1 to a hydrothermal reaction;

step 3: subjecting the solid material obtained after separation of materials from the hydrothermal reaction to drying and roasting in sequence, thereby preparing the lanthanum oxycarbonate catalyst.

8. The method of the embodiment 7, wherein the temperature in step 1 is within a range of 1° C.-20° C., preferably 5° C.-18° C., more preferably 8° C.-12° C.

9. The method of the embodiment 7 or 8, wherein the alkaline solution in step 1 is a sodium hydroxide solution with a concentration of 5 wt %-20 wt %, wherein the addition amount of the alkaline solution per minute is within a range of 0.01-1.5 g in terms of sodium hydroxide, relative to per kg of the lanthanum-containing compound solution;

preferably, the sodium hydroxide solution is added till the obtained mixed material has a pH of 9-13, preferably 10-12.

10. The method of any one of the embodiments 7-9, wherein the method further comprising: stirring the mixed material at a temperature not higher than 20° C. prior to the hydrothermal reaction.

11. The method of any of the embodiments 7-10, wherein the method further comprising: subjecting the mixed material to an ultrasonic treatment prior to the hydrothermal reaction;

preferably, the conditions of ultrasonic treatment comprise: a power of 200 W-1,000 W, a frequency of 20 kHz-120 kHz, a time of 20 min-100 min, and a temperature of 25° C.-60° C.

12. The method of any one of the embodiments 7-11, wherein the lanthanum compound in step 1 is a water-soluble lanthanum salt, preferably selected from the group consisting of lanthanum chloride, lanthanum chlorate and lanthanum nitrate;

preferably, the concentration of lanthanum element in the lanthanum-containing compound solution is within a range of 0.05 wt %-10 wt %, preferably 0.2 wt %-5 wt %, more preferably 0.3 wt %-0.7 wt %.

13. The method of any of the embodiments 7-12, wherein the conditions of hydrothermal reaction in step 2 comprise: a temperature of 150° C.-200° C., and a time of 12 h-100 h;

preferably, the separation in step 3 is carried out under a temperature not higher than 20° C.

14. The lanthanum oxycarbonate catalyst prepared with the method of any one of the embodiments 7-13.

15. A use of the lanthanum oxycarbonate catalyst according to any one of the embodiments 1-6 and 14 in the methane oxidative coupling reaction for producing hydrocarbons containing 2 or more carbon atoms.

16. A method for preparing hydrocarbons containing 2 or more carbon atoms with methane comprising: subjecting the methane and the lanthanum oxycarbonate catalyst of any one of the embodiments 1-6 and 14 to a contact reaction in the presence of oxygen gas under the conditions of methane oxidative coupling reaction; alternatively, preparing a lanthanum oxycarbonate catalyst with the method according to any one of the embodiments 7-13, then subjecting the methane and the obtained lanthanum oxycarbonate catalyst to a contact reaction in the presence of oxygen gas under the conditions of methane oxidative coupling reaction.

17. The method of the embodiment 16, wherein a molar ratio of the used amounts of methane and oxygen gas is within a range of 2-10:1, preferably 3-8:1;

and/or, the temperature of the contact reaction is within a range of 450° C.-650° C.; and/or the hourly space velocity of methane is within a range of 30,000 mL/(g·h)-150,000 mL/(g·h).

The invention will be described in detail below with reference to the examples. In the following examples, the drying box with a model number DHG-9030A was produced by the Shanghai Yiheng Scientific Instrument Co., Ltd.

The muffle furnace with a model number CWF1100 was manufactured by the Carbolite Corporation in the United Kingdom.

The SEM images were analyzed and characterized by the field emission environment scanning electron microscope with a model number XL-30 manufactured by the FEI CORPORATION in the United States of America (USA).

The length and diameter of the rod-shaped catalyst were measured based on the SEM images.

The side lengths, interior angles $\angle A$ and $\angle B$ and thickness of the substantially parallelepiped catalyst were measured by using the scanning electron microscope equipped with a measurement scaleplate.

The mass ratio between the lanthanum oxycarbonate with a substantially parallelepiped structure and the lanthanum oxycarbonate with a rod-shaped structure was calculated based the area ratio of the two morphologies of catalysts on the SEM images, the mass ratios calculated based on 5 electron microscope fields were averaged, the average was rounded off to obtain an integer, which was used as mass ratio between the lanthanum oxycarbonate with a substantially parallelepiped structure and the lanthanum oxycarbonate with a rod-shaped structure in the prepared product.

The analysis of the reaction product composition was carried out through a gas chromatograph with a model number 7890A commercially available from the Agilent Technologies Inc.

The calculation method of methane conversion rate was as follows:

methane conversion rate = amount of methane consumed by reaction/initial amount of methane × 100%.

The calculation method of the ethylene selectivity was as follows:

ethylene selectivity = amount of methane consumed by the produced ethylene/aggregate consumption of methane × 100%.

The calculation method of the ethane selectivity was as follows:

ethane selectivity = amount of methane consumed by the produced ethane/aggregate consumption of methane × 100%.

The calculation method of the propane selectivity was as follows:

$$propane\ selectivity = amount\ of\ methane\ consumed\ by\ the$$
$$produced\ propane/aggregate\ consumption\ of\ methane \times 100\%.$$

The calculation method of the propylene selectivity was as follows:

$$propylene\ selectivity = amount\ of\ methane\ consumed\ by\ the$$
$$produced\ propylene/aggregate\ consumption\ of\ methane \times 100\%.$$

The selectivity of hydrocarbons containing 2 or more carbon atoms comprises the sum of ethylene, ethane, propylene, propane and higher hydrocarbons.

The calculation method of the C2 hydrocarbon yield was as follows:

$$C2\ hydrocarbon\ yield =$$
$$methane\ conversion\ rate \times (ethane\ selectivity + ethylene\ selectivity).$$

The calculation method of the yield of hydrocarbons containing 2 or more carbon atoms was as follows:

$$yield\ of\ hydrocarbons\ containing\ 2\ or\ more\ carbon\ atoms =$$
$$methane\ conversion\ rate \times selectivity\ of$$
$$hydrocarbons\ containing\ 2\ or\ more\ carbon\ atoms.$$

Example 1

6 g of lanthanum nitrate hexahydrate and 351 g of deionized water were accurately weighted and added into a beaker, the concentration of lanthanum element was 0.55 wt %, the temperature was maintained at 10° C., the stirring was carried out with a magnetic stirrer at a stirring rate of 780 rpm, until the lanthanum nitrate was completely dissolved, the stirring rate was then reduced to 250 rpm, the sodium hydroxide solution with a concentration of 10 wt % was added, the adding rate in terms of sodium hydroxide was 0.02 g/min, it corresponded to that 0.056 g of sodium hydroxide was added per minute into per kg of lanthanum nitrate aqueous solution till the precipitation of the solid substance, the stirring rate was subsequently increased to 850 rpm, the sodium hydroxide was further added until a pH of the system reached 11.6, the dropwise adding of sodium hydroxide solution was stopped, the mixed material was obtained, the temperature was maintained at 10° C. and the mixed material was further stirred at a rotational speed of 650 rpm for 10 min, the mixed material was placed in an ultrasonic cleaner and subjected to an ultrasonic treatment for 80 min at an ultrasonic power of 400 W, an ultrasonic frequency of 24 kHz and a temperature of 28° C., the solution was transferred to a polytetrafluoro-lined hydrothermal kettle, and subjected to a static aging at 160° C. for 24 h, after the hydrothermal kettle was cooled to room temperature, the solid material was centrifuged by means of a centrifuge at a temperature of 10° C. and a rotational speed of 8,500 rpm, the solid material was washed with deionized water until a pH of the washing solution was neutral, the obtained solid was dried at 80° C. for 12 h, and roasted in air at 500° C. for 3 h to prepare the catalyst.

FIG. 1 illustrated an X-Ray Diffraction (XRD) spectrogram of the methane oxidative coupling catalyst, wherein the horizontal coordinate was 2θ, the vertical coordinate was the intensity, when compared with the PXRD database (Bruker Diffrac.Eva, Edition 4.2.1), the material was mainly composed of lanthanum oxycarbonate.

Figure 2:
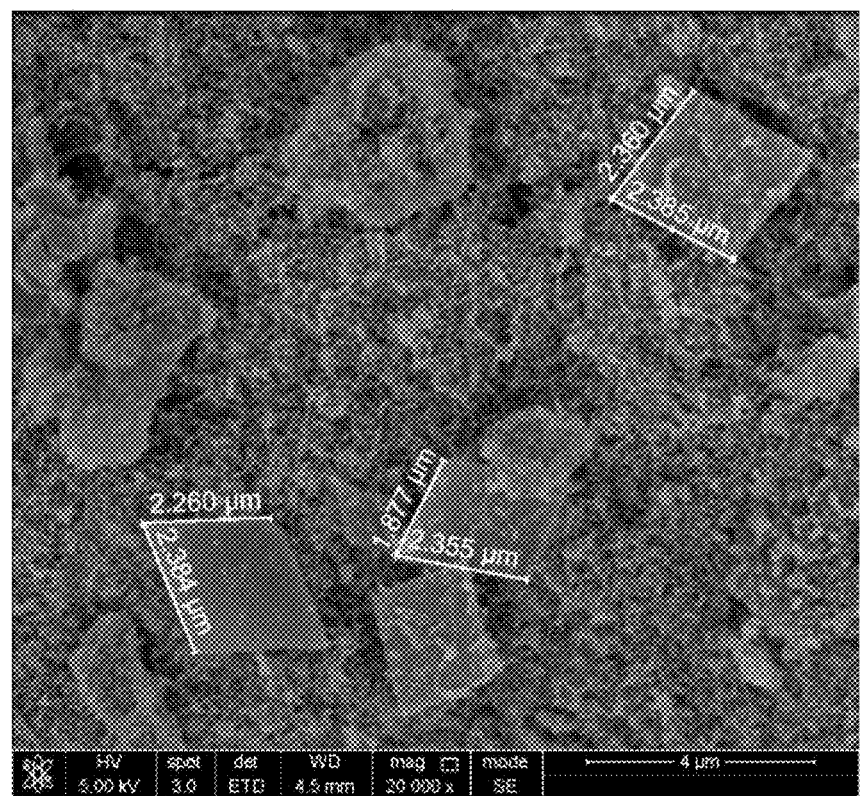
FIG. 2 illustrates a Scanning Electron Microscope (SEM) image of a methane oxidative coupling catalyst prepared in Example 1.
Figure 3:
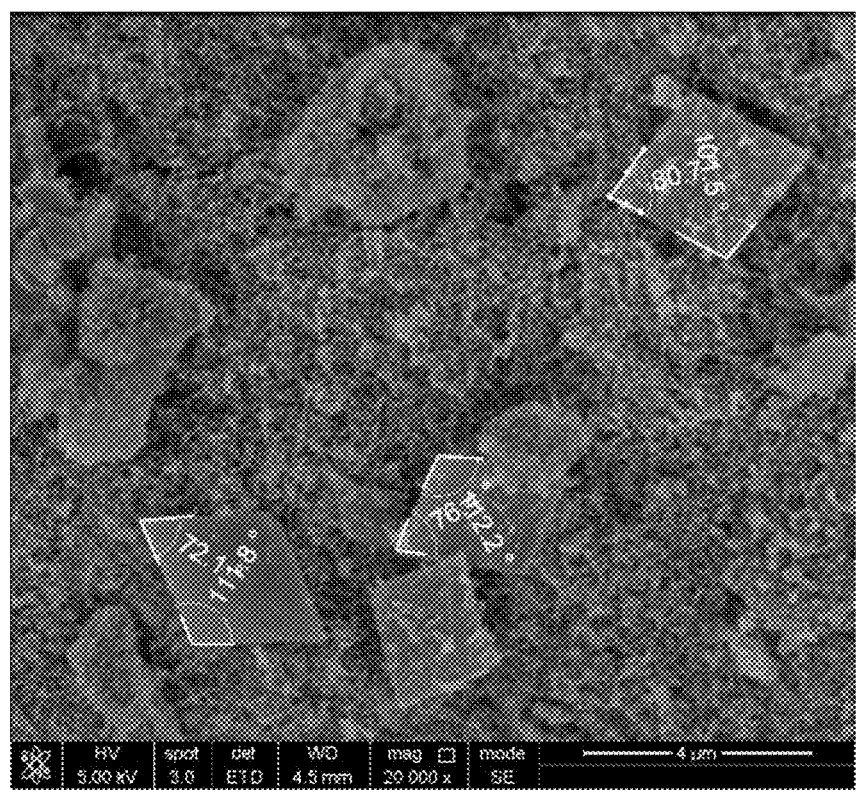
FIG. 3 illustrates a SEM image of a methane oxidative coupling catalyst prepared in Example 1.
Figure 4:
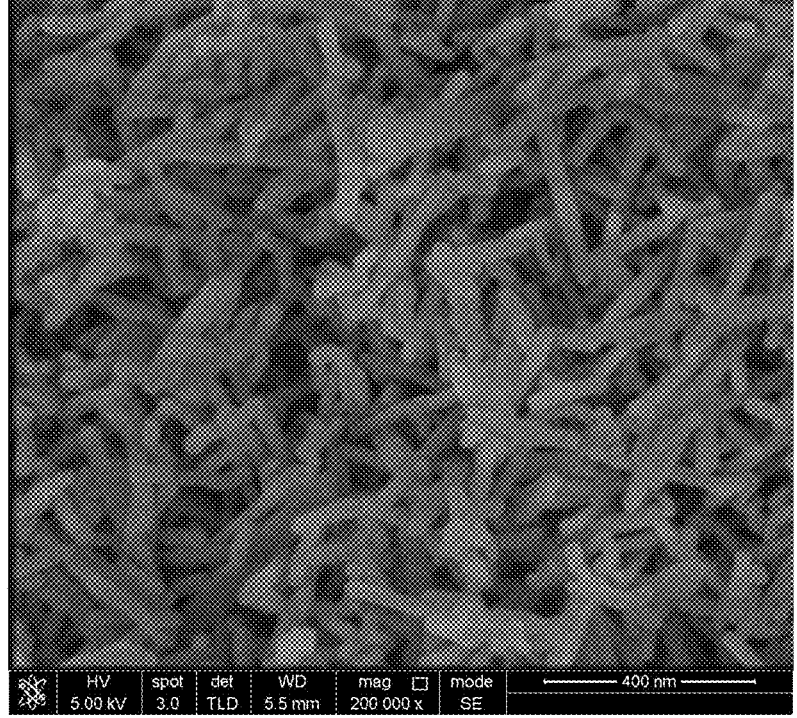
FIG. 4 illustrates a partial enlarged drawing of FIG. 3 illustrating the SEM image of a methane oxidative coupling catalyst prepared in Example 1.

The SEM images of the prepared lanthanum oxycarbonate solid catalyst were as shown in FIG. 2, FIG. 3 and FIG. 4 respectively, wherein FIG. 4 illustrated a partial enlarged drawing of FIG. 3 (the specific enlarged part was as shown by the black square in FIG. 2); as illustrated in the images, the morphologies of said catalyst comprised a substantially parallelepiped lanthanum oxycarbonate and a rod-shaped lanthanum oxycarbonate. Wherein a mass ratio of the substantially parallelepiped lanthanum oxycarbonate to the rod-shaped lanthanum oxycarbonate was 1:6, the substantially parallelepiped lanthanum oxycarbonate had a side length within a range of 1.8 μm-2.5 μm and a thickness within a range of 200 nm-300 nm; the parallelogram lanthanum oxycarbonate had two adjacent interior angles ∠A and ∠B, wherein 70°<∠A<85°, and 175°<(∠A+∠B)<190°; the rod-shaped lanthanum oxycarbonate had a diameter within a range of 25 nm-31 nm and a length within a range of 95 nm-350 nm.

Test Example 1-1

The test example was used to illustrate the first application of the catalyst prepared by Example 1 in a methane oxidative coupling reaction for producing ethylene and ethane.

0.1 g of methane oxidative coupling catalyst was loaded into a fixed bed quartz reactor, the reaction pressure was atmospheric pressure, the molar ratio of methane to oxygen gas was 8:1, the methane hourly space velocity was 120,000 mL/g·h, the methane oxidative coupling reaction temperature was 520° C., the methane conversion rate was 21.3%, the C2 hydrocarbon selectivity was 62.3%, and the C2 hydrocarbon yield was 13.27%; the selectivity of hydrocarbons containing 2 or more carbon atoms was 63.4%, and the yield of hydrocarbons containing 2 or more carbon atoms was 13.5%, the specific results were shown in Table 1.

Test Example 1-2

The test example was used to illustrate the second application of the catalyst prepared by Example 1 in a methane oxidative coupling reaction for producing ethylene and ethane.

0.1 g of methane oxidative coupling catalyst was loaded into a fixed bed quartz reactor, the reaction pressure was atmospheric pressure, the methane hourly space velocity was 68,000 mL/g·h, the molar ratio of methane to oxygen gas was 5:1, the methane oxidative coupling reaction temperature was 600° C., the methane conversion rate was 23.2%, the C2 hydrocarbon selectivity was 54.4%, and the C2 hydrocarbon yield was 10.01%; the selectivity of hydrocarbons containing 2 or more carbon atoms was 58.0%, and the yield of hydrocarbons containing 2 or more carbon atoms was 11.7%, the specific results were shown in Table 1.

Test Examples 1-3

The test example was used to illustrate the third application of the catalyst prepared by Example 1 in a methane oxidative coupling reaction for producing ethylene and ethane.

0.1 g of methane oxidative coupling catalyst was loaded into a fixed bed quartz reactor, the reaction pressure was atmospheric pressure, the methane hourly space velocity was 30,000 mL/g·h, the molar ratio of methane to oxygen gas was 3:1, the methane oxidative coupling reaction temperature was 650° C., the methane conversion rate was 34.1%, the C2 hydrocarbon selectivity was 43.8%, and the C2 hydrocarbon yield was 14.9%; the selectivity of hydrocarbons containing 2 or more carbon atoms was 46.2%, and the yield of hydrocarbons containing 2 or more carbon atoms was 15.7%, the specific results were shown in Table 1.

Test Examples 1-4

The test example was used to illustrate the fourth application of the catalyst prepared by Example 1 in a methane oxidative coupling reaction for producing ethylene and ethane.

0.1 g of methane oxidative coupling catalyst was loaded into a fixed bed quartz reactor, the reaction pressure was atmospheric pressure, the methane hourly space velocity was 142,000 mL/g·h, the molar ratio of methane to oxygen gas was 6:1, the methane oxidative coupling reaction temperature was 450° C., the methane conversion rate was 19.8%, the C2 hydrocarbon selectivity was 56.7%, and the C2 hydrocarbon yield was 11.2%; the selectivity of hydrocarbons containing 2 or more carbon atoms was 58.6%, and the yield of hydrocarbons containing 2 or more carbon atoms was 11.6%, the specific results were shown in Table 1.

Example 2

3 g of lanthanum acetate and 180 g of deionized water were accurately weighted and added into a beaker, the concentration of lanthanum element was 0.73 wt %, the temperature was maintained at 12° C., the stirring was carried out with a magnetic stirrer at a stirring rate of 800 rpm, until the lanthanum acetate was completely dissolved, the sodium hydroxide solution with a concentration of 8 wt % was added under the condition of maintaining stationary, the adding rate in terms of sodium hydroxide was 0.08 g/min, it corresponded to that 0.437 g of sodium hydroxide was added per minute into per kg of lanthanum acetate solution till the precipitation of the solid substance, the stirring rate was subsequently increased to 1,000 rpm, the sodium hydroxide was further added until a pH of the system reached 12, the dropwise adding of sodium hydroxide solution was stopped, the mixed material was obtained, the temperature was maintained at 12° C. and the mixed material was further stirred at a rotational speed of 650 rpm for 30 min, the mixed material was placed in an ultrasonic cleaner and subjected to an ultrasonic treatment for 60 min at an ultrasonic power of 800 W, an ultrasonic frequency of 40 kHz and a temperature of 35° C., the solution was transferred to a polytetrafluoro-lined hydrothermal kettle, and subjected to a static aging at 180° C. for 60 h, after the hydrothermal kettle was cooled to room temperature, the solid material was centrifuged by means of a centrifuge at a temperature of 12° C. and a rotational speed of 7,500 rpm, the solid material was washed with deionized water until a pH of the washing solution was neutral, the obtained solid was dried at 100° C. for 10 h, and roasted in air at 550° C. for 2 h to prepare the catalyst.

The X-Ray Diffraction (XRD) spectrogram of the methane oxidative coupling catalyst illustrated that the material was mainly composed of lanthanum oxycarbonate.

Figure 5:
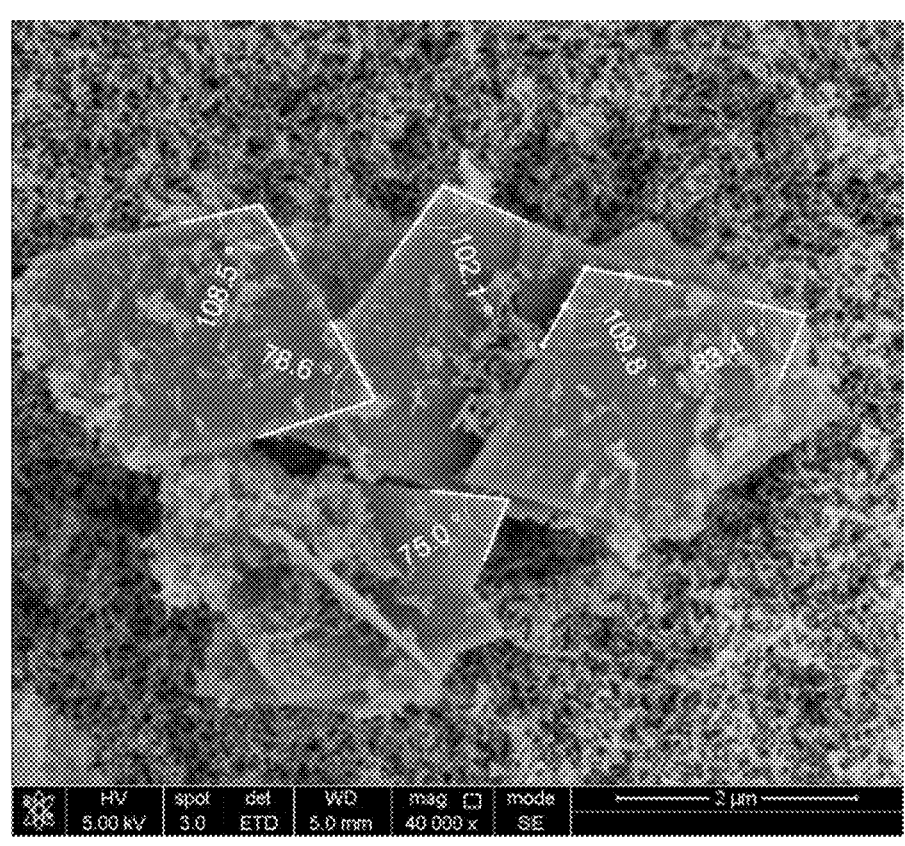
FIG. 5 illustrates a SEM image of a methane oxidative coupling catalyst prepared in Example 2.
Figure 6:
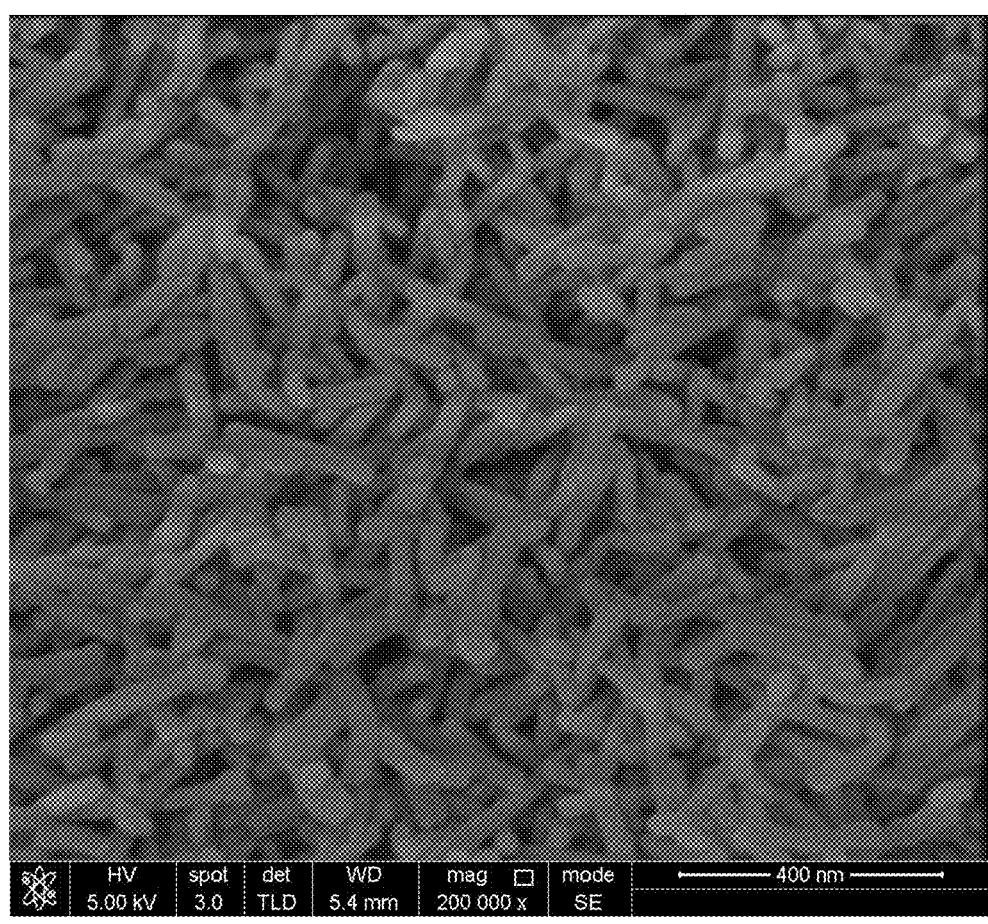
FIG. 6 illustrates a partial enlarged drawing of FIG. 5 illustrating the SEM image of a methane oxidative coupling catalyst prepared in Example 2.

The SEM images of the prepared $La_2O_3CO_3$ solid catalyst were as shown in FIG. 5 and FIG. 6 respectively, wherein FIG. 6 illustrated a partial enlarged drawing of FIG. 5 (the specific enlarged part was as shown by the black square in FIG. 5); as illustrated in the images, the catalyst comprised a substantially parallelepiped lanthanum oxycarbonate and a rod-shaped lanthanum oxycarbonate. Wherein a mass ratio of the substantially parallelepiped lanthanum oxycarbonate to the rod-shaped lanthanum oxycarbonate was 1:12, the substantially parallelepiped lanthanum oxycarbonate had a side length within a range of 1.6 μm-2.6 μm and a thickness within a range of 200 nm-300 nm; the parallelogram lanthanum oxycarbonate had two adjacent interior angles $\angle A$ and $\angle B$, wherein $72°<\angle A<83.5°$, and $170°<(\angle A+\angle B)<193.5°$; the rod-shaped lanthanum oxycarbonate had a diameter within a range of 15 nm-25 nm and a length within a range of 230 nm-450 nm.

Test Example 2-1

The test example was used to illustrate the first application of the catalyst prepared by Example 2 in a methane oxidative coupling reaction for producing ethylene and ethane.

0.1 g of methane oxidative coupling catalyst was loaded into a fixed bed quartz reactor, the reaction pressure was atmospheric pressure, the molar ratio of methane to oxygen gas was 8:1, the methane hourly space velocity was 120,000 mL/g·h, the methane oxidative coupling reaction temperature was 520° C., the methane conversion rate was 20.2%, the C2 hydrocarbon selectivity was 61.2%, and the C2 hydrocarbon yield was 12.4%; the selectivity of hydrocarbons containing 2 or more carbon atoms was 64.3%, and the yield of hydrocarbons containing 2 or more carbon atoms was 13.0%, the specific results were shown in Table 1.

Example 3

5 g of lanthanum nitrate hexahydrate and 250 g of deionized water were accurately weighted and added into a beaker, the concentration of lanthanum element was 0.64 wt %, the temperature was maintained at 8° C., the stirring was carried out with a magnetic stirrer at a stirring rate of 850 rpm, until the lanthanum nitrate was completely dissolved, the stirring rate was then reduced to 100 rpm, the sodium hydroxide solution with a concentration of 8 wt % was added, the adding rate in terms of sodium hydroxide was 0.004 g/min, it corresponded to that 0.0157 g of sodium hydroxide was added per minute into per kg of lanthanum nitrate aqueous solution till the precipitation of the solid substance, the stirring rate was subsequently increased to 1,200 rpm, the sodium hydroxide was further added until a pH of the system reached 11, the dropwise adding of sodium hydroxide solution was stopped, the mixed material was obtained, the temperature was maintained at 8° C. and the mixed material was further stirred at a rotational speed of 800 rpm for 20 min, the mixed material was placed in an ultrasonic cleaner and subjected to an ultrasonic treatment for 70 min at an ultrasonic power of 600 W, an ultrasonic frequency of 30 kHz and a temperature of 40° C., the solution was transferred to a polytetrafluoro-lined hydro-thermal kettle, and subjected to a static aging at 170° C. for 40 h, after the hydrothermal kettle was cooled to room temperature, the solid material was centrifuged by means of a centrifuge at a temperature of 8° C. and a rotational speed of 9,000 rpm, the solid material was washed with deionized water until a pH of the washing solution was neutral, the obtained solid was dried at 90° C. for 12 h, and roasted in air at 450° C. for 4 h to prepare the catalyst.

The X-Ray Diffraction (XRD) spectrogram of the methane oxidative coupling catalyst illustrated that the material was mainly composed of lanthanum oxycarbonate.

The prepared lanthanum oxycarbonate solid catalyst was observed by the scanning electron microscope, as can be seen, the catalyst comprised a substantially parallelepiped lanthanum oxycarbonate and a rod-shaped lanthanum oxycarbonate, wherein a mass ratio of the substantially parallelepiped lanthanum oxycarbonate to the rod-shaped lanthanum oxycarbonate was 1:8, the substantially parallelepiped lanthanum oxycarbonate had a side length within a range of 1.8 μm-3.5 μm and a thickness within a range of 200 nm-400 nm; the parallelogram lanthanum oxycarbonate had two adjacent interior angles $\angle A$ and $\angle B$, wherein $70°<\angle A<85°$, and $173°<(\angle A+\angle B)<184°$; the rod-shaped lanthanum oxycarbonate had a diameter within a range of 16 nm-35 nm and a length within a range of 250 nm-350 nm.

Test Example 3-1

The test example was used to illustrate the first application of the catalyst prepared by Example 3 in a methane oxidative coupling reaction for producing ethylene and ethane.

0.1 g of methane oxidative coupling catalyst was loaded into a fixed bed quartz reactor, the reaction pressure was atmospheric pressure, the molar ratio of methane to oxygen gas was 8:1, the methane hourly space velocity was 120,000 mL/g h, the methane oxidative coupling reaction temperature was 520° C., the methane conversion rate was 21.3%, the C2 hydrocarbon selectivity was 59.8%, and the C2 hydrocarbon yield was 12.74%; the selectivity of hydrocarbons containing 2 or more carbon atoms was 62.7%, and the yield of hydrocarbons containing 2 or more carbon atoms was 13.4%, the specific results were shown in Table 1.

Example 4

2.4 g of lanthanum nitrate hexahydrate and 240 g of deionized water were accurately weighted and added into a beaker, the concentration of lanthanum element was 0.32 wt %, the temperature was maintained at 20° C., the stirring was carried out with a magnetic stirrer at a stirring rate of 1,000 rpm, until the lanthanum nitrate was completely dissolved, the stirring rate was then reduced to 80 rpm, the sodium hydroxide solution with a concentration of 10 wt % was added, the adding rate in terms of sodium hydroxide was 0.3 g/min, it corresponded to that 1.24 g of sodium hydroxide was added per minute into per kg of lanthanum nitrate solution till the precipitation of the solid substance, the stirring rate was subsequently increased to 1,300 rpm, the sodium hydroxide was further added until a pH of the system reached 12.5, the dropwise adding of sodium hydroxide solution was stopped, the mixed material was obtained, the temperature was maintained at 20° C. and the mixed material was further stirred at a rotational speed of 650 rpm for 40 min, the mixed material was placed in an ultrasonic cleaner and subjected to an ultrasonic treatment for 30 min at an ultrasonic power of 1,000 W, an ultrasonic frequency of 15 kHz and a temperature of 50° C., the solution was transferred to a polytetrafluoro-lined hydrothermal kettle, and subjected to a static aging at 200° C. for 12 h, after the hydrothermal kettle was cooled to room temperature, the solid material was centrifuged by means of a centrifuge at a temperature of 20° C. and a rotational speed of 9,000 rpm, the solid material was washed with deionized water until a pH of the washing solution was neutral, the obtained solid was dried at 60° C. for 24 h, and roasted in air at 600° C. for 2 h to prepare the catalyst.

The X-Ray Diffraction (XRD) spectrogram of the methane oxidative coupling catalyst illustrated that the material was mainly composed of lanthanum oxycarbonate.

The prepared lanthanum oxycarbonate solid catalyst was observed by the scanning electron microscope, as can be seen, the catalyst comprised a substantially parallelepiped lanthanum oxycarbonate and a rod-shaped lanthanum oxycarbonate, wherein a mass ratio of the substantially parallelepiped lanthanum oxycarbonate to the rod-shaped lanthanum oxycarbonate was 1:9, the substantially parallelepiped lanthanum oxycarbonate had a side length within a range of 2 μm-4.5 μm and a thickness within a range of 250 nm-380 nm; the parallelogram lanthanum oxycarbonate had two adjacent interior angles $\angle A$ and $\angle B$, wherein $72°<\angle A<85°$, and $172°<(\angle A+\angle B)<188°$; the rod-shaped lanthanum oxycarbonate had a diameter within a range of 20 nm-40 nm and a length within a range of 150 nm-300 nm.

Test Example 4-1

The test example was used to illustrate the first application of the catalyst prepared by Example 4 in a methane oxidative coupling reaction for producing ethylene and ethane.

0.1 g of methane oxidative coupling catalyst was loaded into a fixed bed quartz reactor, the reaction pressure was atmospheric pressure, the molar ratio of methane to oxygen gas was 8:1, the methane hourly space velocity was 120,000 mL/g·h, the methane oxidative coupling reaction temperature was 520° C., the methane conversion rate was 19.8%, the C2 hydrocarbon selectivity was 59.6%, and the C2 hydrocarbon yield was 11.8%; the selectivity of hydrocarbons containing 2 or more carbon atoms was 62.4%, and the yield of hydrocarbons containing 2 or more carbon atoms was 12.4%, the specific results were shown in Table 1.

Example 5—Addition Rate of the Sodium Hydroxide Solution 6 g of lanthanum nitrate hexahydrate and 351 g of deionized water were accurately weighted and added into a beaker, the concentration of lanthanum element was 0.55 wt %, the temperature was maintained at 10° C., the stirring was carried out with a magnetic stirrer at a stirring rate of 780 rpm, until the lanthanum nitrate was completely dissolved, the stirring rate was then reduced to 100 rpm, the sodium hydroxide solution with a concentration of 10 wt % was added, the adding rate in terms of sodium hydroxide was 0.5 g/min, it corresponded to that 1.4 g of sodium hydroxide was added per minute into per kg of lanthanum nitrate aqueous solution till the precipitation of the solid substance, the stirring rate was subsequently increased to 850 rpm, the sodium hydroxide was further added until a pH of the system reached 11.6, the dropwise adding of sodium hydroxide solution was stopped, the mixed material was obtained, the temperature was maintained at 10° C. and the mixed material was further stirred at a rotational speed of 800 rpm for 10 min, the mixed material was placed in an ultrasonic cleaner and subjected to an ultrasonic treatment for 40 min at an ultrasonic power of 400 W, an ultrasonic frequency of 24 kHz and a temperature of 28° C., the solution was transferred to a polytetrafluoro-lined hydrothermal kettle, and subjected to a static aging at 160° C. for 24 h, after the hydrothermal kettle was cooled to room temperature, the solid material was centrifuged by means of a centrifuge at a temperature of 10° C. and a rotational speed of 8,500 rpm, the solid material was washed with deionized water until a pH of the washing solution was neutral, the obtained solid was dried at 80° C. for 12 h, and roasted in air at 500° C. for 3 h to prepare the catalyst.

The X-Ray Diffraction (XRD) spectrogram of the methane oxidative coupling catalyst illustrated that the material was mainly composed of lanthanum oxycarbonate.

The prepared lanthanum oxycarbonate solid catalyst was observed by the scanning electron microscope, as can be seen, the catalyst comprised a substantially parallelepiped lanthanum oxycarbonate and a rod-shaped lanthanum oxycarbonate, wherein a mass ratio of the substantially parallelepiped lanthanum oxycarbonate to the rod-shaped lanthanum oxycarbonate was 1:27, the substantially parallelepiped lanthanum oxycarbonate had a side length within a range of 1.9 μm-2.6 μm and a thickness within a range of 100 nm-250 nm; the parallelogram lanthanum oxycarbonate had two adjacent interior angles ∠A and ∠B, wherein 70°<∠A<86°, and 173°<(∠A+∠B)<186°; the rod-shaped lanthanum oxycarbonate had a diameter within a range of 19 nm-35 nm and a length within a range of 150 nm-400 nm.

Test Example 5-1

The test example was used to illustrate an application of the catalyst prepared by Example 5 in a methane oxidative coupling reaction for producing ethylene and ethane.

0.1 g of methane oxidative coupling catalyst was loaded into a fixed bed quartz reactor, the reaction pressure was atmospheric pressure, the molar ratio of methane to oxygen gas was 8:1, the methane hourly space velocity was 120,000 mL/g·h, the methane oxidative coupling reaction temperature was 520° C., the methane conversion rate was 18.6%, the C2 hydrocarbon selectivity was 62.6%, and the C2 hydrocarbon yield was 11.6%; the selectivity of hydrocarbons containing 2 or more carbon atoms was 65.1%, and the yield of hydrocarbons containing 2 or more carbon atoms was 12.1%, the specific results were shown in Table 1.

Example 6—the Ultrasonic Treatment Was Not Performed 6 g of lanthanum nitrate hexahydrate and 351 g of deionized water were accurately weighted and added into a beaker, the concentration of lanthanum element was 0.55 wt %, the temperature was maintained at 10° C., the stirring was carried out with a magnetic stirrer at a stirring rate of 780 rpm, until the lanthanum nitrate was completely dissolved, the stirring rate was then reduced to 90 rpm, the sodium hydroxide solution with a concentration of 10 wt % was added, the adding rate in terms of sodium hydroxide was 0.02 g/min, it corresponded to that 0.056 g of sodium hydroxide was added per minute into per kg of lanthanum nitrate aqueous solution till the precipitation of the solid substance, the stirring rate was subsequently increased to 950 rpm, the sodium hydroxide was further added until a pH of the system reached 11.6, the dropwise adding of sodium hydroxide solution was stopped, the mixed material was obtained, the temperature was maintained at 10° C. and the mixed material was further stirred at a rotational speed of 850 rpm for 90 min, the solution was transferred to a polytetrafluoro-lined hydrothermal kettle, and subjected to a static aging at 160° C. for 24 h, after the hydrothermal kettle was cooled to room temperature, the solid material was centrifuged by means of a centrifuge at a temperature of 10° C. and a rotational speed of 8,500 rpm, the solid material was washed with deionized water until a pH of the washing solution was neutral, the obtained solid was dried at 80° C. for 12 h, and roasted in air at 500° C. for 3 h to prepare the catalyst.

The X-Ray Diffraction (XRD) spectrogram of the methane oxidative coupling catalyst illustrated that the material was mainly composed of lanthanum oxycarbonate.

The prepared lanthanum oxycarbonate solid catalyst was observed by the scanning electron microscope, as can be seen, the catalyst comprised a substantially parallelepiped lanthanum oxycarbonate and a rod-shaped lanthanum oxycarbonate, wherein a mass ratio of the substantially parallelepiped lanthanum oxycarbonate to the rod-shaped lanthanum oxycarbonate was 1:18, the substantially parallelepiped lanthanum oxycarbonate had a side length within a range of 1.8 μm-2.6 μm and a thickness within a range of 200 nm-300 nm; the parallelogram lanthanum oxycarbonate had two adjacent interior angles ∠A and ∠B, wherein 72°<∠A<85°, and 170°<(∠A+∠B)<185°; the rod-shaped lanthanum oxycarbonate had a diameter of 24 nm-41 nm and a length of 24 nm-390 nm.

Test Example 6

The test example was used to illustrate the application of the catalyst prepared by Example 6 in a methane oxidative coupling reaction for producing ethylene and ethane.

0.1 g of methane oxidative coupling catalyst was loaded into a fixed bed quartz reactor, the reaction pressure was atmospheric pressure, the molar ratio of methane to oxygen gas was 8:1, the methane hourly space velocity was 120,000 mL/g·h, the methane oxidative coupling reaction temperature was 520° C., the methane conversion rate was 19.9%, the C2 hydrocarbon selectivity was 60.4%, and the C2 hydrocarbon yield was 12%; the selectivity of hydrocarbons containing 2 or more carbon atoms was 63.5%, and the yield of hydrocarbons containing 2 or more carbon atoms was 12.6%, the specific results were shown in Table 1.

Example 7

6 g of lanthanum nitrate hexahydrate and 351 g of deionized water were accurately weighted and added into a beaker, the concentration of lanthanum element was 0.55 wt %, the temperature was maintained at 10° C., the stirring was carried out with a magnetic stirrer at a stirring rate of 780 rpm, until the lanthanum nitrate was completely dissolved, the stirring rate was then reduced to 40 rpm, the sodium hydroxide solution with a concentration of 10 wt % was added, the adding rate in terms of sodium hydroxide was 0.02 g/min, it corresponded to that 0.056 g of sodium hydroxide was added per minute into per kg of lanthanum nitrate aqueous solution till the precipitation of the solid substance, the stirring rate was subsequently increased to 1,350 rpm, the sodium hydroxide was further added until a pH of the system reached 11.6, the dropwise adding of sodium hydroxide solution was stopped, the mixed material was obtained, the temperature was maintained at 10° C. and the mixed material was further stirred at a rotational speed of 800 rpm for 10 min, the mixed material was placed in an ultrasonic cleaner and subjected to an ultrasonic treatment for 80 min at an ultrasonic power of 400 W, an ultrasonic frequency of 24 kHz and a temperature of 28° C., the solution was transferred to a polytetrafluoro-lined hydrothermal kettle, and subjected to a static aging at 160° C. for 24 h, after the hydrothermal kettle was cooled to room temperature, the solid material was centrifuged by means of a centrifuge at a room temperature (~25° C.) and a rotational speed of 8,500 rpm, the solid material was washed with deionized water until a pH of the washing solution was neutral, the obtained solid was dried at 80° C. for 12 h, and roasted in air at 500° C. for 3 h to prepare the catalyst.

The X-Ray Diffraction (XRD) spectrogram of the methane oxidative coupling catalyst illustrated that the material was mainly composed of lanthanum oxycarbonate.

The prepared lanthanum oxycarbonate solid catalyst was observed by the scanning electron microscope, as can be seen, the catalyst comprised a substantially parallelepiped lanthanum oxycarbonate and a rod-shaped lanthanum oxycarbonate, wherein a mass ratio of the substantially parallelepiped lanthanum oxycarbonate to the rod-shaped lanthanum oxycarbonate was 1:42, the substantially parallelepiped lanthanum oxycarbonate had a side length within a range of 1.9 μm-3.5 μm and a thickness within a range of 100 nm-250 nm; the parallelogram lanthanum oxycarbonate had two adjacent interior angles $\angle A$ and $\angle B$, wherein $71°<\angle A<86°$, and $171°<(\angle A+\angle B)<185°$; the rod-shaped lanthanum oxycarbonate had a diameter within a range of 25 nm-35 nm and a length within a range of 120 nm-350 nm.

Test Example 7

The test example was used to illustrate an application of the catalyst prepared by Example 7 in a methane oxidative coupling reaction for producing ethylene and ethane.

0.1 g of methane oxidative coupling catalyst was loaded into a fixed bed quartz reactor, the reaction pressure was atmospheric pressure, the molar ratio of methane to oxygen gas was 8:1, the methane hourly space velocity was 120,000 mL/g·h, the methane oxidative coupling reaction temperature was 520° C., the methane conversion rate was 20.5%, the C2 hydrocarbon selectivity was 58.3%, and the C2 hydrocarbon yield was 11.95%; the selectivity of hydrocarbons containing 2 or more carbon atoms was 61.5%, and the yield of hydrocarbons containing 2 or more carbon atoms was 12.6%, the specific results were shown in Table 1.

Comparative Example 1

6 g of lanthanum nitrate hexahydrate and 351 g of deionized water were accurately weighted and added into a beaker, the concentration of lanthanum element was 0.55 wt %, the temperature was maintained at room temperature (~25° C.), the stirring was carried out with a magnetic stirrer at a stirring rate of 780 rpm, until the lanthanum nitrate was completely dissolved, the sodium hydroxide solution with a concentration of 10 wt % was added, the adding rate in terms of sodium hydroxide was 0.02 g/min, it corresponded to that 0.056 g of sodium hydroxide was added per minute into per kg of lanthanum nitrate aqueous solution until a pH of the system reached 11.6, the dropwise adding of sodium hydroxide solution was stopped, the temperature was maintained at room temperature (~25° C.) and the mixed material was further stirred for 10 min, the mixed material was placed in an ultrasonic cleaner and subjected to an ultrasonic treatment for 80 min at an ultrasonic power of 400 W, an ultrasonic frequency of 24 kHz and a temperature of 28° C., the solution was transferred to a polytetrafluoro-lined hydrothermal kettle, and subjected to a static aging at 160° C. for 24 h, after the hydrothermal kettle was cooled to room temperature, the solid material was centrifuged by means of a centrifuge at a room temperature (~25° C.) and a rotational speed of 8,500 rpm, the solid material was washed with deionized water until a pH of the washing solution was neutral, the obtained solid was dried at 80° C. for 12 h, and roasted in air at 500° C. for 3 h to prepare the catalyst.

The prepared lanthanum oxycarbonate solid catalyst was observed by the scanning electron microscope, as can be seen, the obtained product was a rod-shaped lanthanum oxycarbonate, which had a diameter within a range of 25 nm-40 nm and a length within a range of 100 nm-350 nm. Because the conditions during the catalyst nucleation and growth were not precisely controlled, the solid product merely comprised the rod-shaped lanthanum oxycarbonate.

Comparative Test Example 1

The comparative test example was used to illustrate the first application of the catalyst prepared by the Comparative Example 1 in a methane oxidative coupling reaction.

0.1 g of methane oxidative coupling catalyst was loaded into a fixed bed quartz reactor, the reaction pressure was atmospheric pressure, the molar ratio of methane to oxygen gas was 8:1, the methane hourly space velocity was 120,000 mL/gh, the methane oxidative coupling reaction temperature was 520° C., the methane conversion rate was 18%, the selectivity of ethylene and ethane was 49%, and the C2 hydrocarbon yield was 8.82%, the specific results were shown in Table 1.

Comparative Test Example 2

The comparative test example was used to illustrate the second application of the catalyst prepared by the Comparative Example 1 in a methane oxidative coupling reaction.

0.1 g of methane oxidative coupling catalyst was loaded into a fixed bed quartz reactor, the reaction pressure was atmospheric pressure, the molar ratio of methane to oxygen gas was 8:1, the methane hourly space velocity was 120,000 mL/g·h, the methane oxidative coupling reaction temperature was 550° C., the methane conversion rate was 20%, the selectivity of ethylene and ethane was 60.3%, and the C2 hydrocarbon yield was 12.06%, the specific results were shown in Table 1.

TABLE 1

| Catalysts | Reaction temperature ° C. | Ratio of methane to oxygen gas / | Methane hourly space velocity ml/g · h | Methane conversion rate % | C2 hydro-carbon selectivity % | C2 hydrocarbon yield % | Selectivity of hydrocarbons containing 2 or more carbon atoms % | Yield of hydrocarbons containing 2 or more carbon atoms % |
|---|---|---|---|---|---|---|---|---|
| Example 1 | 520 | 8:1 | 120000 | 21.3 | 62.3 | 13.27 | 63.4 | 13.5 |
| | 600 | 5:1 | 68000 | 23.2 | 54.4 | 10.01 | 58.0 | 11.7 |
| | 650 | 3:1 | 30000 | 34.1 | 43.8 | 14.90 | 46.2 | 15.7 |
| | 450 | 6:1 | 142000 | 19.8 | 56.7 | 11.20 | 58.6 | 11.6 |
| Example 2 | 520 | 8:1 | 120000 | 20.2 | 61.2 | 12.36 | 64.3 | 13.0 |
| Example 3 | 520 | 8:1 | 120000 | 21.3 | 59.8 | 12.74 | 62.7 | 13.4 |
| Example 4 | 520 | 8:1 | 120000 | 19.8 | 59.6 | 11.80 | 62.4 | 12.4 |
| Example 5 | 520 | 8:1 | 120000 | 18.6 | 62.6 | 11.64 | 65.1 | 12.1 |
| Example 6 | 520 | 8:1 | 120000 | 19.9 | 60.4 | 12.02 | 63.5 | 12.6 |
| Example 7 | 520 | 8:1 | 120000 | 20.5 | 58.3 | 11.95 | 61.5 | 12.6 |
| Comparative Example 1 | 520 | 8:1 | 120000 | 18.0 | 49.0 | 8.82 | / | / |
| Comparative Example 2 | 550 | 8:1 | 120000 | 20.0 | 60.3 | 12.06 | / | / |

As shown in Table 1, when the methane oxidative coupling catalyst for producing ethylene and ethane prepared according to the present invention is used in the methane oxidative coupling reaction, the similar C2 hydrocarbon yields can be obtained in the methane oxidative coupling reaction for producing ethylene and ethane at a temperature 30° C. lower than the reaction temperature of the catalyst merely comprising a rod-shaped lanthanum oxycarbonate, it demonstrate that the methane oxidative coupling catalyst of the present invention has high activity at a lower reaction temperature.

Moreover, the lanthanum oxycarbonate catalyst is capable of producing a selectivity of C2 hydrocarbon of 50% or more when controlling the methane hourly space velocity within a range of 30,000 mL/(g·h)–150,000 mL/(g·h) and controlling the ratio of methane to the oxygen gas to be 5-8:1, or even producing the selectivity of C2 hydrocarbon of 60% or more under the optimized conditions, thus the selectivity of C2 hydrocarbon is high; in addition, the catalyst has a low selectivity of the byproducts carbon monoxide and carbon dioxide, which reduces the occurrence of deep oxidation reactions, decreases the transient heat release, lowers the difficulty in the heat removal operations after amplification of the reactor, the catalyst produces a high selectivity of C2 hydrocarbon under the condition of high hourly space velocity, thereby providing a technical support for the industrial application of methane oxidative coupling reactions for producing hydrocarbons containing 2 or more carbon atoms.

Further, the present inventors compare the performance of the lanthanum oxycarbonate catalysts prepared by the Examples with the performance of the rod-shaped catalysts prepared by the Literature Hui-Lin Wan, et al (Structure Sensitivity of La$_2$O$_2$CO$_3$ Catalysts in the Oxidative Coupling of Methane, *ACS Catal.*, 2015, No. 5, pp. 1663-1674).

1) The specific evaluation conditions: the total hourly space velocity is 30,000 mL/(g·h), the methane hourly space velocity is 22,500 mL/(g·h), a molar ratio of methane to oxygen gas is 3:1, and the temperature is 500° C.

The Literature: the methane conversion ratio is 30.5%, the C2 hydrocarbon selectivity is 48.6%, the C2 hydrocarbon yield is 14.8%;

the lanthanum oxycarbonate catalyst in Example 1 of the present invention: the methane conversion ratio is 33.5%, the C2 hydrocarbon selectivity is 44.9%, the C2 hydrocarbon yield is 15.04%.

As can be seen, the catalysts provided by the present invention exhibit higher catalytic performance under the same conditions.

2) The temperature required for the catalysts to achieve the C2 hydrocarbon yield of 12%, when the methane hourly space velocity is 120,000 mL/(g·h), and a molar ratio of methane to oxygen gas is 8:1.

The literature: 550° C.;

the lanthanum oxycarbonate catalyst in Example 1 of the present invention: 520° C.

As can be seen, the catalyst of the present invention can achieve the C2 hydrocarbon yield of 12% at 520° C., while the rod-shaped catalyst of the Literature mentioned above achieves the C2 hydrocarbon yield at 550° C. under the same conditions, thus the temperature of the catalyst of the present invention is 30° C. lower than the temperature of the rod-shaped catalyst in the Literature.

Furthermore, the inventors have also performed stability tests on the lanthanum oxycarbonate catalysts prepared in the aforementioned Examples, the results indicate that the catalysts provided by the present invention still have stable properties after 550 h of service life test under the conditions comprising a ratio of methane to oxygen gas being 2-10:1 (preferably 3-8:1), a reaction temperature within a range of 450° C.-650° C., and the methane hourly space velocity within a range of 30,000 mL/(g·h)–150,000 mL/(g·h).

The above content describes in detail the preferred embodiments of the present invention, but the invention is not limited thereto. A variety of simple modifications can be made in regard to the technical solutions of the invention within the scope of the technical concept of the invention, including a combination of individual technical features in any other suitable manner, such simple modifications and combinations thereof shall also be regarded as the content disclosed by the present invention, each of them falls into the protection scope of the present invention.

The invention claimed is:

1. A lanthanum oxycarbonate catalyst, wherein the lanthanum oxycarbonate catalyst comprises a substantially parallelepiped lanthanum oxycarbonate and a rod-shaped lanthanum oxycarbonate, wherein two adjacent interior angles of the substantially parallelepiped lanthanum oxycarbonate are ∠A and ∠B, wherein 60°<∠A<90° and 170°<(∠A+∠B) <195°.

2. The lanthanum oxycarbonate catalyst of claim 1, wherein the substantially parallelepiped lanthanum oxycarbonate is at least 0.01 wt % of a total weight of the lanthanum oxycarbonate catalyst.

3. The lanthanum oxycarbonate catalyst of claim 1, wherein a side length of the substantially parallelepiped is within a range of 1 μm-5 μm; and/or, the substantially parallelepiped lanthanum oxycarbonate has a thickness within a range of 100 nm-500 nm; and/or, $60° < \angle A < 90°$ and $175° < (\angle A + \angle B) < 185°$.

4. The lanthanum oxycarbonate catalyst of claim 1, wherein a mass ratio of the substantially parallelepiped lanthanum oxycarbonate to the rod-shaped lanthanum oxycarbonate is within a range of 1:1-100.

5. The lanthanum oxycarbonate catalyst of claim 1, wherein the rod-shaped lanthanum oxycarbonate has a length of 50 nm-500 nm and a diameter of 15 nm-40 nm.

6. A method for preparing the lanthanum oxycarbonate catalyst of claim 1, comprising:

step 1: adding an alkaline solution into a lanthanum-containing compound solution at a temperature of 1-20° C. to form a mixture;

step 2: subjecting the mixture obtained from step 1 to a hydrothermal reaction;

step 3: subjecting the solid material obtained the mixture from step 2 to drying and roasting in sequence, obtaining the lanthanum oxycarbonate catalyst.

7. The method of claim 6, wherein the alkaline solution in step 1 is a sodium hydroxide solution with a concentration of 5 wt %-20 wt % of sodium hydroxide, wherein the alkaline solution is added at a rate of 0.01-1.5 g per minute of sodium hydroxide, relative to per kg of the lanthanum-containing compound solution.

8. The method of claim 6, wherein the method further comprising: stirring the mixed material at a temperature not higher than 20° C. prior to the hydrothermal reaction.

9. The method of claim 6, wherein the method further comprising: subjecting the mixed material to an ultrasonic treatment prior to the hydrothermal reaction.

10. The method of claim 6, wherein the lanthanum compound in step 1 is a water-soluble lanthanum salt; and/or, a concentration of lanthanum element in the lanthanum-containing compound solution is within a range of 0.05 wt %-10 wt %.

11. The method of claim 6, wherein the hydrothermal reaction in step 2 is carried out at a temperature of 150° C.-200° C. for 12 h-100 h; and/or, the separation in step 3 is carried out under a temperature not higher than 20° C.

12. A method for preparing hydrocarbons containing 2 or more carbon atoms with methane comprising: contacting methane and the lanthanum oxycarbonate catalyst of claim 1 in the presence of oxygen gas to carry out a methane oxidative coupling reaction.

13. The method of claim 12, wherein the methane oxidative coupling reaction is carried out at a molar ratio of methane and oxygen gas is within a range of 2-10:1; and/or, a temperature within a range of 450° C.–650° C.; and/or a hourly space velocity of methane within a range of 30,000 mL/(g·h)–150,000 mL/(g·h).

14. The lanthanum oxycarbonate catalyst of claim 1, wherein the substantially parallelepiped lanthanum oxycarbonate is 0.1-50 wt % of a total weight of the lanthanum oxycarbonate catalyst.

15. The lanthanum oxycarbonate catalyst of claim 1, wherein the substantially parallelepiped lanthanum oxycarbonate is 0.2-45 wt % of a total weight of the lanthanum oxycarbonate catalyst.

16. The lanthanum oxycarbonate catalyst of claim 1, wherein the substantially parallelepiped lanthanum oxycarbonate is 0.6-40 wt % of a total weight of the lanthanum oxycarbonate catalyst.

17. The lanthanum oxycarbonate catalyst of claim 1, wherein a mass ratio of the substantially parallelepiped lanthanum oxycarbonate to the rod-shaped lanthanum oxycarbonate is within a range of 1:2-50.

18. The lanthanum oxycarbonate catalyst of claim 1, wherein a mass ratio of the substantially parallelepiped lanthanum oxycarbonate to the rod-shaped lanthanum oxycarbonate is within a range of 1:5-40.

19. The method of claim 6, wherein the temperature in step 1 is within a range of 5° C.-18° C.

20. The method of claim 6, wherein the temperature in step 1 is within a range of 8° C.-12° C.

21. The method of claim 7, wherein, in step 1, the sodium hydroxide solution is added till the mixture has a pH of 9-13.

22. The method of claim 7, wherein, in step 1, the sodium hydroxide solution is added till the mixture has a pH of 10-12.

23. The method of claim 9, wherein the ultrasonic treatment is carried out at a power of 200 W-1,000 W, a frequency of 20 kHz-120 kHz, for a time of 20 min-100 min, and at a temperature of 25° C.-60° C.

24. The method of claim 6, wherein the lanthanum compound in step 1 is selected from the group consisting of lanthanum chloride, lanthanum chlorate, and lanthanum nitrate; and/or, the concentration of lanthanum element in the lanthanum-containing compound solution is within a range of 0.2 wt %-5 wt %.

25. The method of claim 6, wherein the concentration of lanthanum element in the lanthanum-containing compound solution is within a range of 0.3 wt %-0.7 wt %.

26. The method of claim 12, wherein a molar ratio of methane and oxygen gas is within a range of 3-8:1 in the methane oxidative coupling reaction.

* * * * *